United States Patent [19]

Provancal et al.

[11] Patent Number: 6,126,927
[45] Date of Patent: Oct. 3, 2000

[54] METHOD OF MAKING ANTIPERSPIRANT POWDERS

[75] Inventors: Stephen Provancal, Elmhurst; Richard Oryszczak, Palatine, both of Ill.; Philip P. Angelone, Jr., Wilmington; Nancy M. Karassik, Concord, both of Mass.

[73] Assignee: The Gillette Company, Boston, Mass.

[21] Appl. No.: 09/100,081

[22] Filed: Jun. 19, 1998

[51] Int. Cl.[7] .............................. A61K 7/32; A61K 7/34; A61K 7/38; A61K 31/74; A61K 7/00

[52] U.S. Cl. ................................ 424/65; 424/66; 424/68; 424/78.02; 424/78.05; 424/78.07; 424/78.08; 424/400; 424/401

[58] Field of Search ................................ 424/65, 66, 68, 424/78.02, 78.05, 78.07, 78.08, 400, 401

[56] References Cited

U.S. PATENT DOCUMENTS

| 4,775,528 | 10/1988 | Callaghan et al. | 424/66 |
|---|---|---|---|
| 4,980,167 | 12/1990 | Harashima et al. | 424/401 |
| 5,628,989 | 5/1997 | Harashima et al. | 424/65 |
| 5,643,558 | 7/1997 | Provancal et al. | 424/66 |
| 5,654,362 | 8/1997 | Schulz, Jr. et al. | 524/862 |
| 5,725,836 | 3/1998 | Rouanet | 423/462 |

FOREIGN PATENT DOCUMENTS

| WO 98/00097 | 1/1998 | WIPO . |
|---|---|---|
| WO 98/00104 | 1/1998 | WIPO . |

*Primary Examiner*—Shelley A. Dodson
*Attorney, Agent, or Firm*—Fish & Richardson P.C.

[57] ABSTRACT

A method of making an antiperspirant powder is provided, including mixing a silicone rubber powder solution with an antiperspirant salt in a liquid carrier to form a uniform liquid mixture; and drying the liquid mixture to form an antiperspirant powder.

20 Claims, No Drawings

METHOD OF MAKING ANTIPERSPIRANT POWDERS

BACKGROUND OF THE INVENTION

The invention relates to methods of making antiperspirant powders.

Antiperspirant compositions containing a spheroid silicone rubber powder having an average particle size in the range of 0.1 to 200 μm are disclosed in U.S. Pat. No. 5,628,989, the full disclosure of which is incorporated by reference herein. These compositions are formed by mixing the silicone rubber powder with an antiperspirant salt and other additives.

SUMMARY OF THE INVENTION

The invention features a method for processing finely divided silicone rubber powders to form antiperspirant powders. Using this method, preferred antiperspirant powders exhibit little agglomeration and minimal static charge build-up. Moreover, the antiperspirant powder exhibits good antiperspirant efficacy and provides an aesthetic feeling when applied to the skin.

In one aspect, the invention features a method of making an antiperspirant powder including mixing a solution of a silicone rubber powder with an antiperspirant salt in a liquid carrier to form a uniform liquid mixture, and drying the liquid mixture to form an antiperspirant powder.

In preferred embodiments, the antiperspirant powder is provided in the form of an aqueous solution and the silicone rubber powder is provided in the form of an aqueous suspension. The silicone rubber powder solution comprises silicone rubber powder, a stabilizing surfactant, a non-crosslinking silicone oil, and an inorganic powder. The antiperspirant salt is selected from the group consisting of aluminum salts and aluminum-zirconium salts. The drying conditions are selected to produce an antiperspirant powder having a moisture content of from about 0.1 to 15% by weight and an average particle size of from 0.1 to 200 μm. The drying step includes spray drying the mixture. The method also includes adding a volatile silicone oil to the antiperspirant powder after drying. The solids content of the silicone rubber powder solution is from 5 to 80% by weight and the concentration of the antiperspirant salt solution is from about 2 to 80% by weight.

The invention also features antiperspirant and deodorant compositions including the antiperspirant powder.

The term "solution", as used herein, both with regard to the silicone polymer and the antiperspirant salt, is meant to include solutions, suspensions, emulsions and mixtures of the polymer or salt in any suitable solvent or carrier phase, including but not limited to water, alcohols, and polyhydric alcohols, e.g., propylene and dipropylene glycol.

Other features and advantages of the invention will be apparent from the following Detailed Description and the claims.

DESCRIPTION OF THE PREFERRED EMBODIMENTS

In preferred methods, the solution of the silicone rubber powder, e.g., an aqueous suspension containing a spheroid silicone rubber powder, is mixed with a solution, e.g., an aqueous solution, of an antiperspirant salt. The mixture is then dried to form a fine, dry powder. The powder can be used as an antiperspirant, or an antiperspirant composition can be formed by adding other additives.

Suitable solutions of silicone rubber polymer contain a silicone rubber that, when dried with the antiperspirant salt solution, will yield an antiperspirant powder that can be applied to the skin and will have desired aesthetic and antiperspirant properties. Preferred solutions contain less than 90% by weight of the silicone powder, more preferably 5 to 80% by weight, most preferably 40 to 70%. The silicone rubber particles generally have an average particle size of from about 1 to 50 μm, preferably about 1 to 20 μm.

Preferred silicone rubber powders are formed from an addition reaction curable silicone rubber composition consisting primarily of diorganopolysiloxane which contains a vinyl group bonded to silicon, diorganopolysiloxane which contains hydrogen bonded to silicon, and platinum catalyst. A preferred composition includes an organopolysiloxane which contains at least two intramolecular low molecular weight alkenyl groups, an organopolysiloxane which contains at least two intramolecular silicon bonded hydrogen atoms and a platinum compound catalyst. The JIS A hardness of the silicone rubber formed using this composition is from 20 to 80, preferably from 25 to 65.

If the silicone rubber powder is provided in the form of an aqueous suspension, the aqueous suspension is prepared by uniformly mixing, emulsifying and curing the silicone rubber composition with one or more nonionic, anionic and/or cationic surfactants suitable for use in cosmetic compositions. Preferably the suspension includes from 0.1 to 20 parts by weight of the surfactant per 100 parts by weight of the silicone rubber, more preferably from 0.5 to 10 parts by weight of the surfactant. Aqueous phase thickeners, e.g., cellulose, polyethylene, polycarbonate, polyacrylate, and alkanolamide derived materials, may also be used to stabilize the dispersions.

The silicone rubber powder solution may contain emulsifying and stabilizing surfactants suitable for cosmetic applications, antimicrobial agents, non-crosslinking silicone oils, and fine inorganic powders.

Suitable fine inorganic powders include: silicon oxide, titanium oxide, zinc oxide, aluminum oxide, zirconium oxide, antimony oxide, boron nitride, and aluminum nitrides, sulfides or chlorides. Preferably these powders have an average particle size that is less than one tenth that of the average particle size of the silicone rubber powder, and a surface area greater than 10 m$^2$.

Suitable non-crosslinking silicone oils include any such oils that do not participate in the addition curing reaction of the silicone rubber and that can be incorporated into the silicone rubber composition described above.

Suitable antiperspirant salt solutions are those that, when dried with the silicone rubber powder solution, will yield a powder that can be applied to the skin and that will have desired aesthetic and antiperspirant properties. Preferred antiperspirant salts are any of the conventional aluminum salts and aluminum-zirconium salts known to be useful in antiperspirant compositions. These salts include aluminum hydroxy halides (e.g., aluminum chlorohydrate), and mixtures or complexes thereof with zirconyl oxyhalides and zirconyl hydroxyhalides (e.g., aluminum-zirconium chlorohydrate). Preferred aluminum salts are those having the general formula $Al_2(OH)_{6-a}X_a$ wherein X is Cl, Br, I or $NO_3$, and a is about 0.3 to about 4, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e., X is Cl) and a is about 1, such that the aluminum to chlorine mole ratio is about 1.9:1 to 2.1:1. Preferred aluminum-zirconium salts are mixtures or complexes of the above described salts with zirconium salts of the formula $ZrO(OH)_{2-pb}Y_b$ wherein Y is Cl, Br, I, $NO_3$ or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$ wherein b is about 1 to 2, preferably about 1.2 to about 1.9. The preferred aluminum-zirconium salts have an Al:Zr ratio of about 1.7 to about 12.5, most preferably about 2 to about 8, and a metal:X+Y ratio of about 0.73 to about 2.1, preferably about 0.9 to 1.5. A preferred salt is aluminum-zirconium chlorohydrate (i.e., X and Y are Cl) which has an Al:Zr ratio of about 2 to about 8 and a metal:Cl ratio of about 0.9 to 2.1. Such complexes may also contain a neutral amino acid, preferably glycine, typically with a Zr:Gly ratio of about 1:1 to 1:4.

Some preferred antiperspirant salt solutions, and methods of their manufacture, are described in U.S. Pat. Nos. 4,775,528 and 5,643,558, the full disclosures of which are incorporated herein by reference. The efficacy of the antiperspirant salt can be enhanced by heating the solution, as described in U.S. Pat. No. 5,643,558. As disclosed in U.S. Pat. No. 5,643,558, a preferred method of preparing aqueous solutions of enhanced efficacy antiperspirant salts includes heating a 5 to 18% aqueous solution of aluminum salt, preferably aluminum chlorohydrate, at a sufficient temperature and for a sufficient time to provide an HPLC peak 4 to peak 3 area ratio of at least 0.5, preferably at least 0.7, and most preferably at least 0.9, with at least 70% of the aluminum contained in these peaks. The aqueous solution may be obtained by diluting a standard commercially available 50% salt solution with water to the desired concentration, which is preferably 8 to 15%. The temperature and time of heating may be adjusted as necessary to achieve the desired degree of conversion of the antiperspirant to the enhanced state. Generally, longer times are required at lower temperatures. It is preferred to heat above 50° C., more preferably at 70 to 100° C., for at least two hours, more preferably for at least 10 hours or more.

The silicone rubber powder solution and antiperspirant salt solution are mixed, using any desired mixing method, until uniform. The mixture is then dried using conventional drying equipment. The preferred method is spray drying using conventional spray drying equipment which is readily commercially available. However, drying can be performed using any suitable drying method, including freeze-drying, drum drying and other well known techniques. Drying conditions are selected to provide the finished powder with a desired particle size and moisture content. Suitable drying conditions will vary depending upon the equipment used and properties desired, and can be readily determined empirically. Generally, if the drying temperatures are too high, the properties of the antiperspirant salt and/or the silicone polymer may be degraded, while if the temperatures are too low drying may not occur or the moisture content of the antiperspirant powder may be undesirably high.

After drying, preferred antiperspirant powders have a moisture content of from 0.1 to 15%, more preferably 2 to 8%, when measured by % weight loss at 105° C. for 16 hours, and an average particle size of from about 0.1 to 200 μm, more preferably 5 to 60 μm, when measured by laser diffraction. Higher moisture contents will tend to prevent electrostatic charges from building up in the powder, making processing easier, but too much moisture will tend to cause caking or agglomeration. The particle size is selected to provide a desired aesthetic feel and to facilitate processing of the powder into a finished antiperspirant product.

The silicone emulsion and antiperspirant salt solution can be combined in any desired proportions. The desired ratio will be determined by cost considerations, based on the relative costs of the components and the pricing of the product, and on the antiperspirant and aesthetic properties desired of the antiperspirant powder.

The antiperspirant powders can be mixed with other components to provide a desired antiperspirant or deodorant composition. For example, a volatile silicone oil can be added to the antiperspirant powder to provide desired aesthetic properties. Suitable volatile silicone oils include the cyclic polydimethylsiloxanes, also known as cyclomethicones, which have from about 3 to about 7 silicon atoms, and the linear polydimethylsiloxanes, also known as dimethicones, which have from about 2 to about 9 silicon atoms. The linear volatile silicones generally have viscosities of less than about 5 centistokes at 25° C., while the cyclic volatile silicones have viscosities under 10 centistokes. "Volatile" means that the material has a measurable vapor pressure at room temperature. Due to the properties of the silicone polymer used to form the antiperspirant powders, the powders are advantageously capable of absorbing large amounts of volatile silicone oil. Some preferred antiperspirant compositions contain from 1 to 80%, preferably 40 to 70%, volatile silicone oil by weight, based on the total weight of the composition.

EXAMPLE 1

(Formation of Aqueous Suspension of Silicone Rubber Powder)

A first aqueous suspension of powdered silicone rubber (in subsequent examples, "Suspension 1") was prepared by uniformly mixing, emulsifying and curing (as described in U.S. Pat. No. 5,628,989, the following composition (all percentages are weight percent): 58.9% of a dimethylvinyl-terminated dimethylpolysiloxane (viscosity=approx. 400 mPa-S), 3.9% trimethylsiloxy-terminated polymethylhydrogensiloxane (viscosity=approx. 50 mPa-S; ratio of methylhydrogen to dimethyl groups=0.3), 0.006% of a platinum catalyst, 32.6% of deionized water, 0.3% polyoxyethylene (12) alkyl (secondary C12–C14) ether, 0.25% polyoxyethylene (3) alkyl (secondary C12–C14) ether, 0.6% polyoxyethylene (1) alkyl ether, 1.9% polyoxyethylene (4) alkyl ether, 1.3% PEG-20 and 0.3% each of methyl and propyl hydroxy parabens. The JIS A hardness of the cured silicone rubber was 30. The mean particle size was approximately 4.5 to 6 microns. The suspension pH was approximately 6.5 to 7. The non-volatile content of the powdered silicone rubber suspension was 67–67.9% (measured after heating 2 hours at 105° C.)

A second aqueous suspension of powdered silicone rubber (in subsequent examples, "Suspension 2") was prepared by uniformly mixing, emulsifying and curing the following composition (all percentages are weight percent): 59.9% of a dimethylvinyl-terminated dimethylpolysiloxane (viscosity=approx. 400 mPa-S), 3.3% trimethylsiloxy-terminated polymethylhydrogensiloxane (viscosity=approx. 50 mPa-S; ratio of methylhydrogen to dimethyl groups=0.3), 0.006% of a platinum catalyst, 36.2% of deionized water, 0.26% polyoxyethylene (12) alkyl (secondary C12–C14) ether, 0.015% of sodium salt of polyacrylic acid, and 0.3% of phenoxyethanol. The JIS A hardness of the cured silicone rubber was 30. The mean particle size was approximately 5 microns. The suspension pH was approximately 6.5. The non-volatile content of the powdered silicone rubber suspension was 63.5% (measured after heating 2 hours at 105° C.).

EXAMPLE 2
(Formation of Antiperspirant Salt Solution)

An antiperspirant salt solution was formed as follows:

A 10% aqueous solution of aluminum chlorohydrate was heated for about 16–17 hours at 80° C. This solution was then partially concentrated, to a concentration of approximately 50%, by passing it through a thin film evaporator. To about 3 kg of this solution about 2.1 kg of zirconium hydroxy chloride glycinate (a 50% aqueous ZHC gly solution with a Gly:Zr ratio of about 1:1) was added at room temperature and mixed for about 10 minutes. The resulting tetra chlorohydrex glycine, with an Al:Zr ratio of about 3.6:1, when tested by HPLC had more than 80% of aluminum in peaks 3 and 4 and a peak 4 to peak 3 ratio greater than 1.

EXAMPLE 3
(Formation of Antiperspirant Powder)

The suspension of silicone rubber powder formed in Example 1 was mixed until uniform (about 10 minutes using an IKA RW20 DZM mixer) with the antiperspirant salt solution of Example 2, at the following ratios: 1:1, 1:5, 1:10, 1:20, 1:30 and 1:50. Each mixture was spray dried using a Bowen BE994 pilot size spray dryer, at an air pressure of about 50 psi, with inlet and outlet temperatures ranging from 169 to 180° C. and 85 to 105° C., respectively, at rates of from 170 to 230 ml/min. Powders having good aesthetic and handling properties were obtained from each mixture.

Other embodiments are within the claims. For example, although it is preferred that the antiperspirant salt be provided in the form of a solution, the antiperspirant salt could under some circumstances be added directly to the silicone rubber powder solution and mixed to form a uniform liquid mixture.

What is claimed is:

1. A method of making an antiperspirant salt comprising:
   mixing a silicone rubber powder solution with an antiperspirant salt in a liquid carrier to form a uniform liquid mixture; and
   drying the liquid mixture to form an antiperspirant powder.

2. The method of claim 1 wherein the antiperspirant salt is provided in the form of an aqueous solution.

3. The method of claim 2 wherein the silicone rubber powder solution is an aqueous suspension.

4. The method of claim 2 wherein the silicone rubber powder comprises an addition reaction curable silicone rubber composition comprising a diorganopolysiloxane which contains a vinyl group bonded to silicon, a diorganopolysiloxane which contains hydrogen bonded to silicon, and a platinum catalyst.

5. The method of claim 4 wherein the silicone rubber composition comprises an organopolysiloxane which contains at least two intramolecular alkenyl groups, an organopolysiloxane which contains at least two intramolecular silicon bonded hydrogen atoms and a platinum compound catalyst.

6. The method of claim 4 wherein the JIS A hardness of the silicone rubber powder is from about 20 to 80.

7. The method of claim 2 wherein the silicone rubber powder solution comprises silicone rubber powder, a stabilizing surfactant, a non-crosslinking silicone oil, and an inorganic powder.

8. The method of claim 2 wherein the antiperspirant salt is selected from the group consisting of aluminum salts and aluminum-zirconium salts.

9. The method of claim 8 wherein the antiperspirant salt is selected from the group consisting of aluminum hydroxy halides and mixtures or complexes thereof with zirconyl oxyhalides and zirconyl hydroxyhalides.

10. The method of claim 8 wherein the aluminum salt has the general formula $Al_2(OH)_{6-a}X_a$ wherein X is Cl, Br, I or $NO_3$, and a is about 0.3 to about 4, such that the Al to X mole ratio is about 1:1 to 2.1:1.

11. The method of claim 8 wherein the aluminum-zirconium salts comprises a mixture or complex of an aluminum salt having the general formula $Al_2(OH)_{6-a}X_a$ wherein X is Cl, Br, I or $NO_3$, and a is about 0.3 to about 4, such that the Al to X mole ratio is about 1:1 to 2.1:1 with a zirconium salt of the formula $ZrO(OH)_{2-pb}Y_b$ wherein Y is Cl, Br, I, $NO_3$ or $SO_4$, b is about 0.8 to 2, and p is the valence of Y.

12. The method of claim 2 wherein the antiperspirant salt comprises a combination of aluminum chlorhydroxide and zirconyl hydroxy chloride.

13. The method of claim 2 further comprising selecting the drying conditions to produce an antiperspirant powder having a moisture content of from about 0.1 to 15% by weight.

14. The method of claim 2 further comprising selecting the drying conditions to produce an antiperspirant powder having an average particle size of from 0.1 to 200 $\mu$m.

15. The method of claim 2 wherein the drying step comprises spray drying.

16. The method of claim 2 further comprising the step of adding a volatile silicone oil to the antiperspirant powder after drying.

17. The method of claim 2 wherein the solids content of the silicone rubber powder solution is from 5 to 80% by weight.

18. The method of claim 2 wherein the concentration of the antiperspirant salt solution is from about 2 to 80% by weight.

19. The method of claim 10, wherein a is about 1 to 2.

20. The method of claim 11, wherein a is about 1 to 2.

* * * * *